United States Patent
Taeschler et al.

(10) Patent No.: US 10,125,087 B2
(45) Date of Patent: Nov. 13, 2018

(54) METHOD FOR PREPARATION OF N-BUTYL NITRITE

(71) Applicant: LONZA LTD, Visp (CH)

(72) Inventors: Christoph Taeschler, Visp (CH); Ulrich Mayerhoeffer, Visp (CH); Christophe Girard, Sion (CH); Michael Bittel, Visp (CH); Rolf Kalbermatten, Törbel (CH); Claudio Arnold, Brig-Glis (CH); Stefan Garms, Brig-Glis (CH); Christian Schnider, Visp (CH); Stefan Tille, Naters (CH); Manuel Favre, Glis (CH); Guy Raboud, Niedergesteln (CH); Kilian Schnydrig, Mund (CH); Martin Venetz, Brig-Glis (CH); Thomas Eggel, Naters (CH)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 15/747,510

(22) PCT Filed: Sep. 14, 2016

(86) PCT No.: PCT/EP2016/071620
§ 371 (c)(1),
(2) Date: Jan. 25, 2018

(87) PCT Pub. No.: WO2017/046118
PCT Pub. Date: Mar. 23, 2017

(65) Prior Publication Data
US 2018/0251420 A1  Sep. 6, 2018

Related U.S. Application Data

(60) Provisional application No. 62/219,222, filed on Sep. 16, 2015.

(30) Foreign Application Priority Data

Sep. 16, 2015 (EP) .................................... 15185501
Nov. 10, 2015 (EP) .................................... 15193769
Mar. 7, 2016 (EP) .................................... 16158944
Jul. 4, 2016 (EP) .................................... 16177682
Jul. 13, 2016 (EP) .................................... 16179239
Sep. 8, 2016 (EP) .................................... 16187855

(51) Int. Cl.
*C07C 201/04* (2006.01)
*C07C 203/00* (2006.01)
*B01J 19/18* (2006.01)

(52) U.S. Cl.
CPC .......... *C07C 201/04* (2013.01); *B01J 19/1881* (2013.01); *C07C 203/00* (2013.01); *B01J 2219/00033* (2013.01); *B01J 2219/00162* (2013.01); *B01J 2219/00166* (2013.01)

(58) Field of Classification Search
None
See application file for complete search history.

(56) References Cited

U.S. PATENT DOCUMENTS

2003/0149292 A1* 8/2003 Karrer .................. C07C 201/04
558/486
2004/0199003 A1 10/2004 Kudis et al.

OTHER PUBLICATIONS

International Search Report and Written Opinion dated May 12, 2016 from International Application No. PCT/EP2016/071620, 10 Pages.

* cited by examiner

*Primary Examiner* — Samantha L Shterengarts
(74) *Attorney, Agent, or Firm* — MH2 Technology Law Group, LLP

(57) ABSTRACT

The invention discloses a method for the continuous preparation of n-butyl nitrite with a low content of n-butanol comprising the reaction of n-butanol, an acid and $NaNO_2$ in a continuous way, in which the n-butanol, an acid and $NaNO_2$ are mixed in a mixing device which provides for a pressure drop of at least 1 bar; the acid is selected from the group consisting of HCl, $H_2SO_4$, formic acid, methanesulfonic acid, and mixtures thereof; and the amount of HCl is at least 1.02 molar equivalent based on the molar amount of n-butanol.

15 Claims, 1 Drawing Sheet

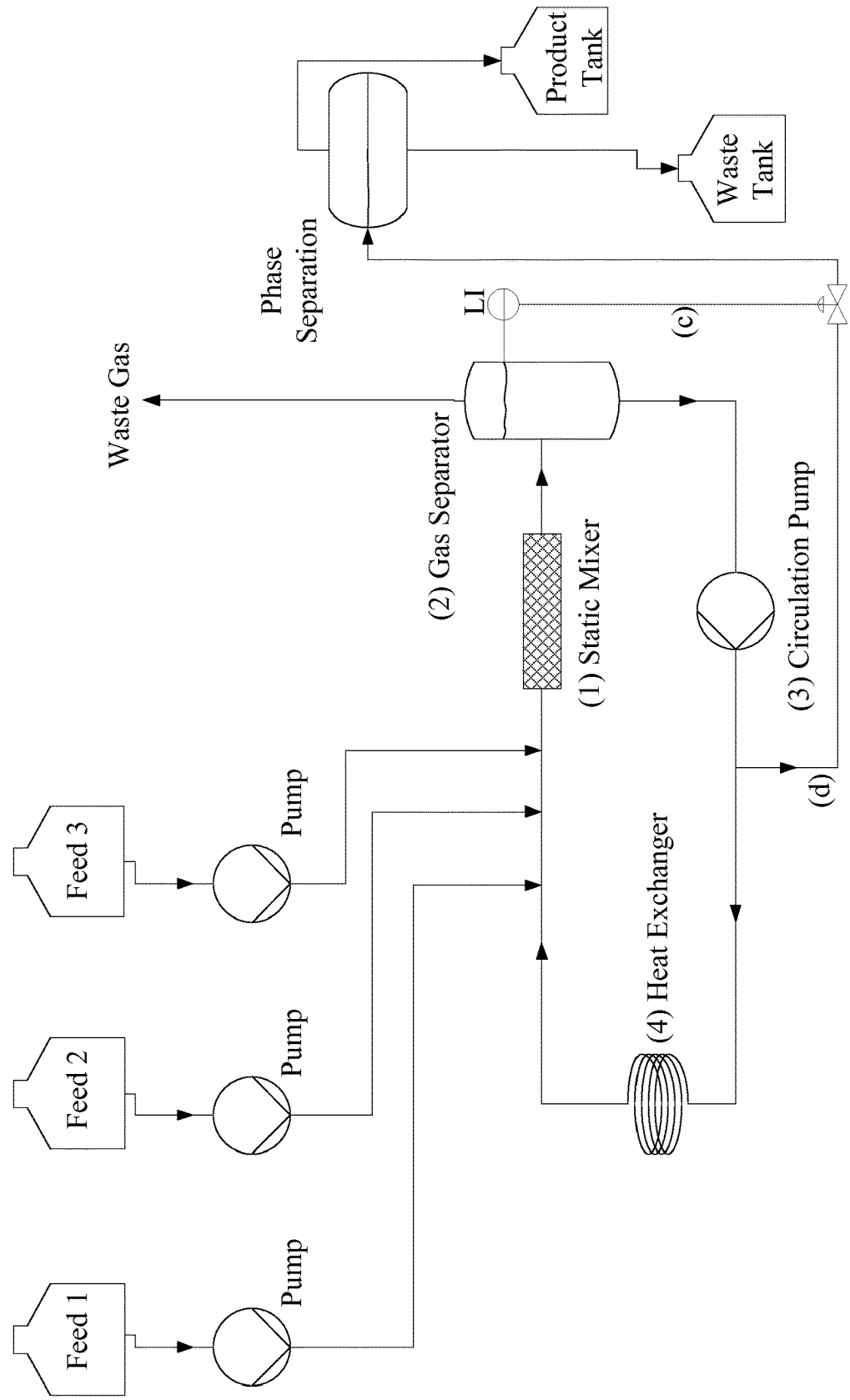

METHOD FOR PREPARATION OF N-BUTYL NITRITE

CROSS-REFERENCE TO RELATED APPLICATIONS

This application is a U.S. National Stage application of PCT/EP2016/071620 filed 14 Sep. 2016, which claims priority to U.S. Provisional Patent Application No. 62/219,222 filed 16 Sep. 2015, European Patent Application No. 15185501.2 filed 16 Sep. 2015, European Patent Application No. 15193769.5 filed 10 Nov. 2015, European Patent Application No. 16158944.5 filed 7 Mar. 2016, European Patent Application No. 16177682.8 filed 4 Jul. 2016, European Patent Application No. 16179239.5 filed 13 Jul. 2016, and European Patent Application No. 16187855.8 filed 8 Sep. 2016, the entire disclosures of which are hereby incorporated by reference in their entireties.

The invention discloses a method for the continuous preparation of n-butyl nitrite with a low content of n-butanol comprising the reaction of n-butanol, an acid and $NaNO_2$ in a continuous way, in which the n-butanol, an acid and $NaNO_2$ are mixed in a mixing device which provides for a pressure drop of at least 1 bar; the acid is selected from the group consisting of HCl, $H_2SO_4$, formic acid, methanesulfonic acid, and mixtures thereof; and the amount of HCl is at least 1.02 molar equivalent based on the molar amount of n-butanol.

BACKGROUND OF THE INVENTION n-Butyl nitrite is useful agent for nitrosation. It can for example be used for the preparation of diazonium residue containing compounds from primary amines.

US 2003/149292 A1 discloses a method for preparing alkyl nitrites RONO wherein R represents a $C_{1-20}$ linear or branched alkyl group; the method consists in gradually and continuously adding in an aqueous medium, an alcohol ROH, a nitrite $MNO_2$, wherein M represents a metal cation, and a strong acid, so as to form continuously said alkyl nitrite, and in continuously drawing off said alkyl nitrite thus formed from the reaction medium. Of the two examples 1 and 2, only example 1 concerns the preparation of n-butyl nitrite, the example discloses a residual n-butanol content in thus prepared n-butyl nitrite of 1.7 to 1.9% (GC), the purity of the n-butyl nitrite is 97 to 98%.

WO 03/014059 A1 discloses a process for continuous preparation of alkyl nitrites and alkyl dinitrites by reaction of an alkanol or a dialkanol with an inorganic nitrite in the presence of at least one mineral acid that does not oxidize nitrite, wherein
(i) the alkanol or dialkanol is mixed with an aqueous solution of the mineral acid using on average not more than 1.01 mol of acid equivalents per mole of hydroxyl group in the alkanol or dialkanol,
(ii) an aqueous solution of the inorganic nitrite is added continuously to the aqueous mixture obtained in (i) in a reaction zone, and
(iii) the organic phase is optionally isolated.
Purities from 98.62% to 99.02% (GC) are reported. Residual butanol content was from 0.77% to 1.01%.

There was a need for a process with high yield of n-butyl nitrite and simultaneously with a low content of n-butanol of 0.7% or lower (GC area %). A low content of residual n-butanol is important because the residual n-butanol interferes in following reactions where the n-butyl nitrite is used as substrate.

Furthermore the process should work with shorter reaction times and/or shorter residence times.

Surprisingly it was found that an increase of the amount of acid improves the yield and lowers the residual content of n-butanol in a continuous reaction. This was unexpected since WO 03/014059 A1 expressly stresses the need for a low amount of acid.

In the following text, if not otherwise stated, the following meanings are used:
ambient pressure usually 1 bar, depending on the weather;
BUOH n-butanol, n-BuOH;
BUONO n-butyl nitrite;
Ex example;
CE comparative example;
RETI residence time;
wt % percent by weight, weight-%, wt-%.

SUMMARY OF THE INVENTION

Subject of the invention is a method for the preparation of n-butyl nitrite;
the method comprises a step STEP1, STEP1 comprises a reaction REAC1, in REAC1 n-butanol, an acid ACI and $NaNO_2$ are reacted;
REAC1 is done in a continuous way;
the n-butanol, ACI and $NaNO_2$ are mixed in a mixing device MIXDEV;
ACI is selected from the group consisting of HCl, $H_2SO_4$, formic acid, methanesulfonic acid, and mixtures thereof;
MIXDEV provides for a pressure drop DELTAP of at least 1 bar; and
the amount of ACI is at least 1.02 molar equivalent, the molar equivalent being based on the molar amount of n-butanol.

BRIEF DESCRIPTION OF THE DRAWINGS

FIG. 1 shows schematically a loop reactor that comprises sequentially (1) a static mixer, (2) a gas-separator, (3) a circulation pump and (4) a heat exchanger, with the outlet of the heat exchanger connected to the inlet of the static mixer, thereby forming the loop reactor, as described in the examples.

DETAILED DESCRIPTION OF THE INVENTION

The three components of REAC1, the n-butanol, ACI and $NaNO_2$, are conveyed through MIXDEV by means of a pump. MIXDEV causes the mixing of the three components, the passage of the three components through MIXDEV causes DELTAP.

Preferably, MIXDEV is a static mixing device or a continuously working micro reactor.

Static mixing devices, e.g. static mixers, are well established and widespread in all fields of chemical process technology. It is characteristically for static mixing devices, that, in contrast to dynamic mixing devices, only the media to be mixed are in motion. The liquids or gases are mixed by pump energy only, while the geometrically strong defined mixing elements in the static mixing devices remain in position. Companies such as Fluitec, Seuzachstrasse, 8413 Neftenbach, Switzerland, or Sulzer Ltd, Neuwiesenstrasse 15, 8401 Winterthur, Switzerland, are well known suppliers among others of such static mixing devices.

Micro reactors, also called microstructured reactors, are devices in which chemical reactions take place in a confinement with typical lateral dimensions below 1 mm; the most typical form of such confinement are microchannels. A micro reactor is a continuous flow reactor. They have been successfully applied in lab, pilot and production scale. E.g. the Fraunhofer Institute for Chemical Technology ICT, Joseph-von-Fraunhofer Strasse 7, 76327 Pfinztal, Germany, develops and offers such micro reactors.

Preferably, the static mixing device has the form of a tube containing means that present obstacles for the flow of the three components and thereby effecting the mixing of the three components.

Preferably, the micro reactor contains micro channels which are arranged in such a way as to effect the mixing.

Preferably, DELTAP is from 1 to 100 bar, more preferably from 1 to 50 bar.

Preferably, in case that MIXDEV is a static mixing device, then DELTAP is from 1 to 10 bar, more preferably from 1 to 5 bar, even more preferably from 1 to 4 bar, especially from 1.5 to 4 bar.

Preferably, in case that MIXDEV is a continuously working micro reactor, then DELTAP is from 5 to 100 bar, more preferably from 5 to 50 bar.

Preferably, the amount of ACI is from 1.02 to 1.5 molar equivalent, more preferably from 1.02 to 1.4 molar equivalent, even more preferably from 1.02 to 1.3 molar equivalent, especially from 1.02 to 1.2 molar equivalent, the molar equivalent being based on the molar amount of n-butanol.

In another embodiment, preferably the amount of ACI is from 1.03 to 1.5 molar equivalent, more preferably from 1.03 to 1.4 molar equivalent, even more preferably from 1.03 to 1.3 molar equivalent, especially from 1.03 to 1.2 molar equivalent, the molar equivalent being based on the molar amount of n-butanol.

Preferably, HCl and $H_2SO_4$ is used as an aqueous solution,

More preferably, HCl is used as an aqueous solution of from 25 to 40 wt %; even more preferably of from 30 to 35 wt %; especially of 33 wt %.

More preferably, $H_2SO_4$ is used as an aqueous solution of from 20 to 40 wt %; even more preferably of from 25 to 35 wt %.

Preferably, ACI is selected from the group consisting of HCl, $H_2SO_4$, formic acid, and mixtures thereof;

more preferably, ACI is HCl or $H_2SO_4$;

even more preferably, ACI is HCl.

Preferably, $NaNO_2$ is used as an aqueous solution;

more preferably, $NaNO_2$ is used as an aqueous solution of from 30 to 50% (w/w); even more preferably of from 35 to 45% (w/w).

Preferably, the amount of $NaNO_2$ is from 1.0 to 3 molar equivalent, more preferably from 1.01 to 2 molar equivalent, even more preferably from 1.02 to 1.5 molar equivalent, especially from 1.03 to 1.4 molar equivalent, more especially from 1.04 to 1.25 molar equivalent, the molar equivalent being based on the molar amount of n-butanol.

The reaction time of REAC1 is from 0.1 sec to 2 h, preferably from 0.1 sec to 1 h, more preferably from 0.1 sec to 30 min, even more preferably from 0.1 sec to 20 min.

Preferably, in case that MIXDEV is a static mixing device, then the reaction time of REAC1 is from 1 min to 2 h, more preferably from 1 min to 1 h, even more preferably from 1 min to 30 min, especially from 1 min to 20 min.

Preferably, in case that MIXDEV is a continuously working micro reactor, then the reaction time of REAC1 is from 0.1 sec to 30 sec, more preferably from 0.1 sec to 20 sec, even more preferably from 0.5 sec to 10 sec.

Preferably, REAC1 is done in a loop shaped device LOOPDEV;

n-Butanol, ACI and $NaNO_2$ are fed into LOOPDEV providing a reaction mixture REACMIX in LOOPDEV;

LOOPDEV comprises MIXDEV and a device CONVDEV for conveyance of REACMIX;

the outlet of MIXDEV is connected to the inlet of CONVDEV and the outlet of CONVDEV is connected to the inlet of MIXDEV, thereby the loop is formed.

Preferably CONVDEV is a pump.

Preferably, LOOPDEV comprises a device HEATDEV for heat exchange.

Preferably, LOOPDEV comprises a device GASSEPDEV gas separation.

More preferably,
    the outlet of HEATDEV is connected to the inlet of MIXDEV,
    the outlet of MIXDEV is connect to the inlet of GASSEPDEV,
    the outlet of GASSEPDEV is connected to the inlet of CONVDEV,
    the outlet of CONVDEV is connected to the inlet of HEATDEV.

Preferably, the three components n-butanol, an acid ACI and $NaNO_2$ are fed into LOOPDEV between HEATDEV and MIXDEV.

The three components n-butanol, an acid ACI and $NaNO_2$ can be fed into LOOPDEV in any spatial sequence with respect to the direction of the flow of REACMIX in LOOPDEV. n-Butanol and ACI can be premixed resulting in a mixture and then can be fed into LOOPDEV in form of said mixture.

Preferably, n-butanol, ACI and $NaNO_2$ are fed separately into LOOPDEV;

more preferably, spatially with respect to the direction of the flow of REACMIX in LOOPDEV, first n-butanol, then ACI and then $NaNO_2$ are fed into LOOPDEV;

in another more preferable embodiment, spatially with respect to the direction of the flow of REACMIX in LOOPDEV, first $NaNO_2$, then ACI and then n-butanol are fed into LOOPDEV.

Preferably, the residence time RETI of REACMIX in LOOPDEV is from 0.1 sec to 2 h, preferably from 0.1 sec to 1 h, more preferably from 0.1 sec to 30 min, even more preferably from 0.1 sec to 20 min.

Preferably, in case that MIXDEV is a static mixing device, then the residence time RETI of REACMIX in LOOP-DEV is from 1 min to 2 h, more preferably from 1 min to 1 h, even more preferably from 1 min to 30 min, especially from 1 min to 20 min.

Preferably, the method comprises a further step STEP2, STEP2 is done after STEP1, in STEP2 an extraction EXTR is done, wherein REACMIX is extracted with water.

After STEP1 REACMIX consists of two phases, an organic phase comprising BUONO and an aqueous phase. BOUNO is isolated by phase separation. BUONO can be used as it is provided by the phase separation.

EXAMPLES

Methods

Chloride content was determined by titration with AgNO$_3$.

CONT is the content of BUONO and the content of n-butanol respectively, given in area % of the GC FID (gas chromatography flame ionization detector) analysis.

Comparative Example CE1, CE2 and CE3

A two-step CSTR (Continuous Stirred Tank Reactor) setup consisting of two reaction vessels was used. The reactants n-butanol, aqueous solution of sodium nitrite 40% (w/w) and aqueous HCl 33% (w/w) were fed into the first reaction vessel. The reaction mixture in the first reaction vessel was stirred. The volume of the reaction mixture in the first reaction vessel was kept at 110 ml by overflow means leading into the second reaction vessel. The reaction mixture in the first reaction vessel was stirred. The volume of the reaction mixture in the second reaction vessel was kept at 200 ml by overflow means leading into a product tank. Initially the first reaction vessel was filled with 33 ml n-butanol and 56 ml of the nitrite. Then the streams of the three reactants were started and fed into the first reaction vessel. This feed resulted in a residence time RETI1 in the first reaction vessel and in a residence time RETI2 in the second reaction vessel. The temperature in both reaction vessels was kept at 20° C. by mantle cooling. After 100 min of feeding the organic phase in the product tank was separated. For analysis of CONT samples of the outlet stream of the second reaction vessel were taken after having run a specific set of parameters for at least 5 times of the average residence time RETI2.

These feed parameters were varied, all parameters and results are summarized in Table 1.

TABLE 1

| | Feeds | | | | | | RETI1 | RETI2 | CONT | |
| | BUOH | | HCl | | Nitrite | | | | BUONO | BUOH |
| CE | [g/min] | eq. | [g/min] | eq. | [g/min] | eq. | [min] | [min] | [%] | [%] |
| CE1 | 3.4 | 1.00 | 6.10 | 1.20 | 8.70 | 1.10 | 6.8 | 8.7 | 98.8 | 0.9 |
| CE2 | 3.4 | 1.00 | 5.35 | 1.05 | 8.70 | 1.10 | 7.1 | 9.0 | 98.9 | 0.9 |
| CE3 | 3.4 | 1.00 | 5.15 | 1.01 | 8.70 | 1.10 | 7.2 | 9.1 | 97.9 | 1.9 |

Examples 4 to 13

A loop reactor was used for the production of BUONO, the loop reactor is shown schematically in FIG. 1 and comprised sequentially (1) a static mixer (inner dimensions=36 mm×176 mm, Fluitec Static Mixer CSE-V-8 Typ E DN40, Fluitec, Seuzachstrasse, 8413 Neftenbach, Switzerland), (2) a gas-separator, (3) a circulation pump and (4) a heat exchanger (plate heat exchanger, 3 m$^2$), the outlet of the heat exchanger was connected to the inlet of the static mixer, thereby forming the loop reactor.

Three feed streams, Feed1, Feed2 and Feed 3, were fed via pumps into the loop reactor between the heat exchanger and the static mixer. The feeds were fed spatially one behind the other in respect to the direction of the flow of the reaction mixture. Between the circulation pump and the heat exchanger an outlet (d) was installed, the outlet leads the product stream into a phase separator in which the upper phase comprising the product was separated from the lower phase comprising the aqueous waste.

When the three feeds were running, representing a constant input into the loop reactor, the outlet was regulated by measuring the level of reaction mixture in the gas separator (LI in FIG. 1) and by maintaining a constant level in the gas separator by regulating the outlet respectively, as illustrated by (c) and (d) in FIG. 1.

The average residence time RETI was adjusted by setting a desired rate of the three feeds and/or by setting the level of the reaction mixture in the gas separator.

The reaction temperature TE was measured between (3) the circulation pump and (4) the heat exchanger.

Initially, the loop reactor was filled with water, the circulation pump was started. Then Feed 1, Feed 2 and Feed 3 were started. Samples of the outlet stream (d) were taken after having run a specific set of parameters for at least 5 times of the average residence time RETI.

Feed 1: NaNO$_2$ as an aqueous solution of sodium nitrite (40% w/w)

Feed 2: HCl as an aqueous HCl33% (w/w)

Feed 3: n-butanol

The parameters and results are given in Table 3.

TABLE 3

| | Feeds | | | | | | | CONT | |
|---|---|---|---|---|---|---|---|---|---|
| Ex | 3: BUOH [kg/h] | 2: HCl [kg/h] | [eq] | 1: NaNO$_2$ [kg/h] | [eq] | TE [° C.] | DELTAP [bar] | RETI [min] | BUOH [%] | BUONO [%] |
| 4  | 166.9 | 256.5 | 1.03  | 408.0 | 1.05  | 22.7 | 1.6 | 9.2  | 0.68 | 99.21 |
| 5  | 166.8 | 256.4 | 1.03  | 408.0 | 1.05  | 25.0 | 1.8 | 9.2  | 0.63 | 99.28 |
| 6  | 167.0 | 256.2 | 1.03  | 408.0 | 1.05  | 23.9 | 1.9 | 9.2  | 0.52 | 99.43 |
| 7  | 49.8  | 76.4  | 1.03  | 122.1 | 1.05  | 15.7 | 2.6 | 30.9 | 0.56 | 99.39 |
| 8  | 167.0 | 256.6 | 1.03  | 407.9 | 1.05  | 24.5 | 2.5 | 9.2  | 0.62 | 99.32 |
| 9  | 199.7 | 307.0 | 1.03  | 488.5 | 1.05  | 19.3 | 2.8 | 7.7  | 0.60 | 99.27 |
| 10 | 168.0 | 257.8 | 1.03  | 410.4 | 1.05  | 19.2 | 2.3 | 9.2  | 0.50 | 99.36 |
| 11 | 168.0 | 258.2 | 1.03  | 418.4 | 1.07  | 19.6 | 2.0 | 9.1  | 0.50 | 99.36 |
| 12 | 140.1 | 219.2 | 1.05  | 358.3 | 1.1   | 19.5 | 2.2 | 10.7 | 0.60 | 99.26 |
| 13 | 167.8 | 256.4 | 1.025 | 408.0 | 1.045 | 23.2 | 3.5 | 5.6  | 0.63 | 99.3  |

The invention claimed is:

1. A method for the preparation of n-butyl nitrite; wherein the method comprises a step STEP1, STEP1 comprises a reaction REAC1, and in REAC1 n butanol, an acid ACI and NaNO$_2$ are reacted;
REAC1 is done in a continuous way;
the n-butanol, ACI and NaNO$_2$ are mixed in a mixing device MIXDEV;
ACI is selected from the group consisting of HCl, H$_2$SO$_4$, formic acid, methanesulfonic acid, and mixtures thereof;
MIXDEV provides for a pressure drop DELTAP of at least 1 bar; and
the amount of ACI is at least 1.02 molar equivalent, the molar equivalent being based on the molar amount of n-butanol.

2. The method according to claim 1, wherein MIXDEV is a static mixing device or a continuously working micro reactor.

3. The method according to claim 1, wherein DELTAP is from 1 to 100 bar.

4. The method according to claim 1, wherein the amount of ACI is from 1.02 to 1.5 molar equivalent.

5. The method according to claim 1, wherein ACI is selected from the group consisting of HCl, H$_2$SO$_4$, formic acid, and mixtures thereof.

6. The method according to claim 1, wherein the amount of NaNO$_2$ is from 1.0 to 3 molar equivalent, the molar equivalent being based on the molar amount of n-butanol.

7. The method according to claim 1, wherein the reaction time of REAC1 is from 0.1 second to 2 hours.

8. The method according to claim 1, wherein REAC1 is done in a loop shaped device LOOPDEV;
n-butanol, ACI and NaNO$_2$ are fed into LOOPDEV providing a reaction mixture REACMIX in LOOPDEV;
LOOPDEV comprises MIXDEV and a device CONVDEV for conveyance of REACMIX; and
the outlet of MIXDEV is connected to the inlet of CONVDEV and the outlet of CONVDEV is connected to the inlet of MIXDEV, thereby the loop is formed.

9. The method according to claim 8, wherein CONVDEV is a pump.

10. The method according to claim 8, wherein LOOPDEV comprises a device HEATDEV for heat exchange.

11. The method according to claim 8, wherein LOOPDEV comprises a device GASSEPDEV gas separation.

12. The method according to claim 11, wherein
the outlet of HEATDEV is connected to the inlet of MIXDEV,
the outlet of MIXDEV is connect to the inlet of GAS SEPDEV,
the outlet of GAS SEPDEV is connected to the inlet of CONVDEV, and
the outlet of CONVDEV is connected to the inlet of HEATDEV.

13. The method according to claim 12, wherein n-butanol, ACI and NaNO$_2$ are fed into LOOPDEV between HEATDEV and MIXDEV.

14. The method according to claim 8, wherein n-butanol, ACI and NaNO$_2$ are fed separately into LOOPDEV.

15. The method according to claim 8, wherein the residence time RETI of REACMIX in LOOPDEV is from 0.1 second to 2 hours.

* * * * *